United States Patent
Saita et al.

[11] Patent Number: 5,158,726
[45] Date of Patent: Oct. 27, 1992

[54] PROCESS FOR PRODUCTION OF CERAMIC SHAPED PRODUCT HAVING GRANULE LAYER ON THE SURFACE AND CERAMIC IMPLANT MATERIAL

[75] Inventors: Kenji Saita, Toyonaka; Susumu Miyazaki, Ibaraki, both of Japan

[73] Assignee: Sumitomo Chemical Company, Limited, Osaka, Japan

[21] Appl. No.: 679,148

[22] Filed: Mar. 28, 1991

Related U.S. Application Data

[60] Continuation of Ser. No. 299,640, Jan. 23, 1989, abandoned, which is a division of Ser. No. 144,183, Jan. 15, 1988, abandoned.

[30] Foreign Application Priority Data

Jan. 20, 1987 [JP] Japan .................. 62-11668

[51] Int. Cl.$^5$ .............................................. C04B 41/87
[52] U.S. Cl. .................................... 264/60; 264/62; 427/2
[58] Field of Search ............... 264/60, 62; 427/419.2, 427/2

[56] References Cited

U.S. PATENT DOCUMENTS

| | | | |
|---|---|---|---|
| 520,868 | 6/1894 | Strusholm | 264/62 |
| 3,575,789 | 4/1971 | Siefert et al. | 264/60 |
| 4,158,684 | 6/1979 | Klawitter et al. | 264/62 |
| 4,223,412 | 9/1980 | Aoyagi et al. | 3/1.9 |
| 4,237,559 | 12/1980 | Borom | 428/303 |
| 4,774,045 | 9/1988 | Kushiada et al. | 264/256 |
| 4,878,914 | 11/1989 | Miwa et al. | 427/2 |

FOREIGN PATENT DOCUMENTS

| | | | |
|---|---|---|---|
| 41854 | 9/1983 | Japan . | |
| 60-118661 | 6/1985 | Japan | 264/62 |

*Primary Examiner*—James Derrington
*Attorney, Agent, or Firm*—Birch, Stewart, Kolasch & Birch

[57] ABSTRACT

A ceramic shaped product comprising a ceramic substrate, a single or multiple layers of ceramic spherical granules on the surface of the substrate, and a process for the production thereof, which comprising arranging spherical granules of a ceramic material on the surface of the ceramic substrate in a single or multiple layers at a state of contacting each other, pouring a slurry of a ceramic powder onto the layer(s) of ceramic spherical granules, followed by sintering. The ceramic shaped product has strong binding between the granules and the plate and also between each granules at wide contact and has an excellent strength, and hence, is useful for various utilities, particularly as an implant such as artificial bones, artificial joints, artificial tooth roots and the like.

7 Claims, 1 Drawing Sheet

PROCESS FOR PRODUCTION OF CERAMIC SHAPED PRODUCT HAVING GRANULE LAYER ON THE SURFACE AND CERAMIC IMPLANT MATERIAL

This application is a continuation of application Ser. No. 07/299,640 filed on Jan. 23, 1989, which a divisional application of Ser. No. 07/144,183, filed on Jan. 15, 1988, both now abandoned.

This invention relates to a process for the production of a ceramic shaped product having a layer(s) of ceramic granules on the surface and a ceramic implant material obtained by said process. More particularly, it relates to a process for the production of a porous ceramic shaped product comprising a single or multiple layers of ceramic granules on the surface wherein the granules are strongly bound each other and also to the ceramic substrate, and a ceramic implant material produced by said process which is useful as artificial materials such as artificial joints, artificial tooth roots and artificial bones in living bodies.

BACKGROUND OF THE INVENTION

There have been known various ceramic shaped products having porous surface which have good affinity to living bodies and comparatively high mechanical strength and hence are mainly used as implant materials, i.e. replacements for various hard tissues in living bodies, such as artificial tooth roots or artificial bones.

However, the known porous ceramic shaped products have small pore diameter and less open cells, and hence, when the porous ceramic shaped products are used as an implant, bone tissue is hardly grown within the cells and further it is difficult to sterilize or clean the cells positioned in the inner region of the products.

There has also been used a porous shaped product having a comparatively large pore size and open cells as an implant material. For example, it is disclosed in Japanese Patent Second Publication (Kokoku) No. 41954/1983 that a clay-like plastic composition comprising granules, an aqueous solution of a binder and naphthalene powder is formed and sintered to form a porous shaped product, and the shaped product is inserted into a dense ceramic tube (outer tube) and sintered by heating to form a ceramic shaped product containing a porous region in inner part thereof. However, the shaped product obtained by this method has a drawback that the binding between each granule and also between the granules and the outer tube is very weak because the binding is effected by sintering at the contact point of the granules. That is, in said product, the binding between the granules and the outer tuber is done at only one point and that between each granule is effected at only 6 to 12 points, and hence, the binding between the granules and the outer tube (substrate), which is effected by sintering, is very weak, and further, the binding between each granule is also insufficient.

SUMMARY OF THE INVENTION

The present inventors have intensively studied to obtain a ceramic shaped product having a porous structure without encountering problems associated with known products, i.e., produce a product having strong binding between the granules and the substrate. The inventors have found that the desired shaped product can be obtained by forming a layer of granules of ceramic material on the surface of the substrate, when said ceramic, material is the same as or similar to the material of the ceramic substrate An object of the invention is to provide a ceramic shaped product having a single or multiple layers of ceramic spherical granules on the surface thereof. Another object of the invention is to provide a process for the production of a ceramic shaped product having a single or multiple layers of ceramic granules on the surface wherein the binding between each ceramic granule and between the ceramic granules and the ceramic substrate is strong. A further object of the invention is to provide a ceramic shaped product having a layer(s) of ceramic granules on the surface which comprises arranging spherical granules of a ceramic material which is the same as or similar to the material of the ceramic substrate so as to form a single or multiple layers on the surface of the substrate, where the ceramic granules in the layer are contacted with the surface of the ceramic substrate, applying thereon a slurry of a ceramic material which is the same as or similar to that of the ceramic substrate on the surface of the substrate, and then sintering the resultant. A still further object of the invention is to provide an implant material comprising a ceramic shaped product having a layer(s) of ceramic granules of the material which is the same as or similar to that of the ceramic substrate on the surface of the substrate. These and other objects and advantages of the invention will be apparent to those skilled in the art from the following description.

DETAILED DESCRIPTION OF THE INVENTION

Figure 1:
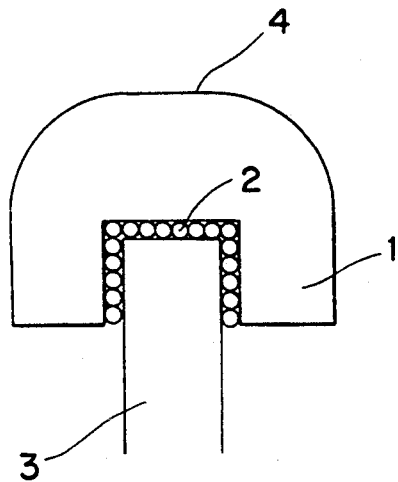
FIG. 1 to 3 are schematic views showing the state of binding of some embodiments of the ceramic shaped products of this invention with bones when the ceramic shaped products of this invention are used as an implant.

The ceramic shaped product of this invention comprises a ceramic substrate and a single or multiple layers of ceramic granules which are composed of a ceramic material the same as or similar to the material of the ceramic substrate, said layer(s) of ceramic granules being strongly bound on the surface of the substrate.

The ceramic substrate used in this invention is a conventional dense ceramic sintered product which is usually used as a structural material and has excellent strength and is prepared from conventional ceramic materials, for example, oxide substances (e.g. alumina, zirconia, etc.) and non-oxide substances (e.g. silicon nitride, silicon carbide, etc.). These conventional materials can be used without specific limitation, but in view of harmlessness to living bodies when used as an implant, alumina and zirconia are particularly preferable.

The ceramic substrate is previously formed into the desired shape by sintering or sintering followed by processing the ceramic material by a conventional method.

The ceramic granules, particularly spherical granules, are composed of a dense ceramic material which is the same as or similar to the material for the ceramic substrate. The size of granules is not specified but may vary depending on the desired pore sizes of the final product, and the granules have usually a size (diameter) of 0.3 to 5.0 mm, preferably 0.5 to 2.0 mm, more preferably 0.7 to 1.2 mm. In order to obtain a shaped product having uniform pore size, it is preferable to use granules having a uniform size. When the size of the ceramic spherical granules is less than 0.3 mm, the shaped product obtained therefrom tends unfavorably to have uneven pore size. For producing a ceramic shaped product useful as an implant material, the ceramic granules have preferably a size (diameter) of 0.5 to 2.0 mm, more preferably 0.7 to 1.2 mm, because when the porous ceramic shaped product produced by using such ceramic granules is used as an implant, new bone is easily penetrated into the gaps of each granules to afford a strong fixation of the implant to the living body.

The slurry used for forming the layer(s) of ceramic spherical granules on the surface of the ceramic substrate comprises a ceramic powder and a binder in a dispersing medium. The starting ceramic powder is the same as or similar to the material for the ceramic substrate, which has a particle size of not more than 5 $\mu$m, preferably not more than 1 $\mu$m. When the starting ceramic powder has a smaller particle size, the slurry is more stable and the ceramic powder is more easily sintered. Thus, the starting ceramic powder has preferably a particle size of not more than 5 $\mu$m, more preferably 0.1 to 1 $\mu$m.

The binder and dispersing medium include any conventional ones which can give a solution of a binder in a medium. For example, when an aqueous medium (e.g. water, hydrochloric acid solution, etc.) is used as a dispersing medium, the binder includes polyvinyl alcohol, polyethylene oxide, hydroxycellulose, and the like, and in case of using a non-aqueous medium (e.g. ethanol, isopropanol, butanol, methyl ethyl ketone, trichloroethylene, etc.), the binder includes polyvinyl butyral, polymethyl methacrylate, cellulose acetate butyrate, and the like.

The slurry can be prepared by a conventional method, for example, by dispersing well the ceramic powder in a solution of a binder in a dispersing medium. The slurry of the ceramic powder should have a viscosity which the slurry can penetrated into the gaps of the ceramic granules.

The optimum viscosity of the slurry may vary depending on the size of ceramic spherical granules, the thickness of the layer(s) to be applied to the substrate, and the like, but the viscosity is usually in the range of 5 to 100 centipoises. The concentration of the binder and ceramic powder to be contained in the slurry is important because the viscosity of the slurry is much effected by the concentration of these components. The ceramic powder is usually contained in the slurry in a concentration of 10 to 30% by weight. The binder is preferably used in the slurry in an amount of 2 to 20 parts by weight per 100 parts by weight of the ceramic powder, but the amount is not critical and the most suitable amount may be determined under taking into consideration the concentration of the ceramic powder and the desired viscosity of the slurry. The slurry of ceramic powder may optionally be incorporated with other conventional additives such as sintering aids, plasticizers, dispersing agents, and the like.

The porous ceramic shaped product having a layer(s) of ceramic granules on the surface can be produced in the following manner.

Firstly, the ceramic spherical granules are arranged on the surface of the ceramic substrate so as to form a layer contacting with the surface of the substrate. The number of layers is not critical and may be selected appropriately in accordance with the utilities of the final product, but is preferably 1 to 10 layers, more preferably 1 to 5 layers, particularly preferably 1 to 3 layers, in view of uniformity of the gap size between each ceramic granules. When the ceramic shaped product is used as an implant material, too much multiple layers are not suitable for sterilization and cleaning thereof, and hence, the number of layers is preferably in the range of 1 to 5 layers.

When the ceramic granules are arranged on a plane surface of the ceramic substrate, or on the surface of cylindrical or angular substrate, it is preferable to use a frame. In case of a substrate having a concave surface, it is easier to arrange the ceramic granules on the surface.

Thereafter, for example, a slurry of the starting ceramic powder is poured onto the surface of the substrate arranged with the ceramic granules whereby the granules are immersed in the slurry, followed by drying. By the drying, the ceramic powder is concentrated and coagulated around the contact points between the granules and substrate and also between each granules. If a frame is used, it is removed at this stage, and then, it is heated to remove the binder and to sinter the ceramic powder by a conventional method to give a ceramic shaped product having a layer(s) of ceramic granules on the surface. The slurry of ceramic powder is not necessarily poured in an amount sufficient to dip the ceramic granules but may be used in an amount sufficient to wet the granules.

According to the process of this invention, the starting ceramic powder is sintered at the contact points between the ceramic granules and the ceramic substrate and also between each granules in the state that the ceramic granules and the ceramic substrate and also each ceramic granules are contacted each other, and hence, the resultant sintered product has a wide contact area between the granules and substrate and also between each granules, and hence, the product has excellent strength.

The ceramic shaped product of this invention may optionally have a coating film of various materials on the surface, by which the surface has good gloss, various colors, hardness, and various affinity to oils or water. The coating film includes that of various materials, such as metals, ceramics, oils and fats, and the like. The coating film can be formed by conventional methods, such as dipping method, coating method, deposition method, CVD method (abbreviation of chemical vapor deposition), PVD method (abbreviation of physical vapor deposition), ion plating method, thermal spraying method, and the like. For example, when a coating film of hydroxyapatite is formed on the surface by plasma spraying method, the ceramic shaped product has improved compatibility with living bodies and hence is suitable for use as an implant material.

One embodiment of utility of the ceramic shaped product of this invention is illustrated by the accompanying drawing.

Figure 2:
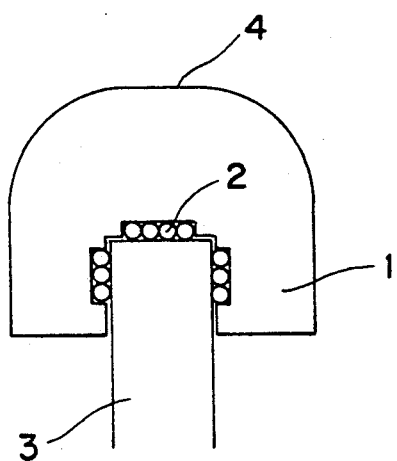
Figure 3:
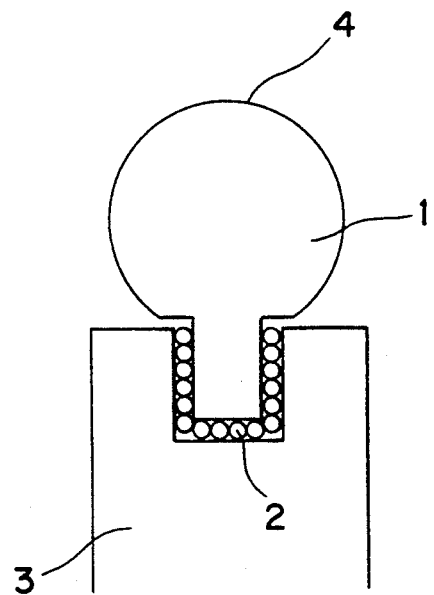

FIG. 1 to 3 show some embodiments of the ceramic shaped product of this invention which is used as an implant for a joint. That is, in said embodiments as an implant, a ceramic substrate 1 is strongly bound with ceramic granules 2, which is well fit and integrated with a bone 3. The face 4 means a sliding face.

By applying the implant to the living bodies, for instance, as an artificial joint or bone, the bone tissue is impregnated and grown in the gaps between each granules and thereby the implant is strongly bound with the bone. The ceramic shaped product may have various shapes suitable for the desired utilities so as to make fit to the shapes of portions to be applied. The products have high strength and are easily sterilized and cleaned.

The present invention can provide ceramic shaped products having a single or multiple layers of ceramic granules on the surface wherein the ceramic granules are strongly bound with the ceramic substrate and hence are useful for various utilities, particularly, as an implant.

This invention is illustrated by the following Examples but should not be construed to be limited thereto. In Examples, "part" means part by weight unless specified otherwise.

EXAMPLE 1

A frame (inner size: 25×25 mm, depth: 8 mm, thickness: 1 mm) is made from paraffin wax. In the frame, a dense sintered plate of alumina [25×25 mm×2 mm (thickness)] is put, and on the plate is arranged spherical granules of a dense sintered product of alumina (diameter: 1 mm) in three layers.

Separately, a slurry of alumina is prepared by mixing fine powder of alumina (AKP-20, manufactured by Sumitomo Chemical Co., Ltd., mean particle size: 0.5 μm) (100 parts), a fine powder of magnesia (Kyowamag® 30, manufactured by Kyowa Kagaku Kogyo K.K., mean particle size: 0.35 μm, which is a sintering aid) (0.2 part), polyvinyl butyral (Esreck® B BLS, manufactured by Sekisui Chemical Co., Ltd., which is a binder) (8 parts), dibutyl phthalate (as a plasticizer) (3.6 parts), glycerin trioleate (as a dispersing agent) (1.7 part), trichloroethylene (as a dispersing medium) (540 parts), and ethanol (as a dispersing medium) (100 parts), and mixing well the mixture with a ball mill for 96 hours.

The slurry thus prepared is poured onto the layers of alumina spherical granules in the frame until the alumina spherical granules are wholly dipped. Thereafter, it is dried at room temperature overnight, and the frame is removed, and then, it is heated at 250° C. for 3 hours to remove the binder, followed by heating further at 1600° C. for one hour to sinter the ceramic.

In the sintered product thus obtained, an alumina layer is formed in the state of crosslinking between the alumina spherical granules and an alumina plate and also between each alumina spherical granules, in which the granules and plate are strongly bound.

EXAMPLE 2

A slurry is prepared by dispersing a mixture of a fine powder of alumina (AKP-20, manufactured by Sumitomo Chemical Co., Ltd., mean particle size: 0.5 μm) (100 parts), a fine powder of magnesia (Kyowamag® 30, manufactured by Kyowa Kagaku Kogyo K.K., mean particle size: 0.35 μm) (0.05 part), polyvinyl alcohol (Poval® 217, manufactured by Kuraray Co., Ltd.) (2 parts), and hydrochloric acid (pH 2) (567 parts) in a water bath with a ultrasonic for 30 minutes.

In the same manner as described in Example 1 except that the above slurry is used, there is prepared a sintered product. In the sintered product, the alumina spherical granules are strongly bound onto the alumina plate.

REFERENCE EXAMPLE 1

A binder solution is prepared by dispersing a mixture of polyvinyl alcohol (Poval® 217, manufactured by Kuraray Co., Ltd, as a binder) (2 parts) and hydrochloric acid (pH 2) (567 parts) in a water bath with a ultrasonic for 30 minutes.

The same alumina spherical granules (4 spheres) as used in Example 1 are arranged on the same alumina plate as used in Example 1, and thereon is poured dropwise the binder solution prepared above, and the resultant is dried overnight. The resultant is heated in the same manner as described in Example 1. In the resulting product, the alumina granules and alumina plate are appeared to be bound, but when it is lightly touched with a finger, they are peeled off.

EXAMPLE 3

A frame (inner diameter: 5 mm, outer diameter: 7 mm, depth: 10 mm) is made from paraffin wax. A round bar of a dense sintered product of alumina (diameter: 3 mm, length: 15 mm) is put at the central region of the frame, and spherical granules of a dense sintered product of alumina (diameter: 1 mm) are filled between the round bar and the frame. Onto the layer of the alumina spherical granules is poured the same slurry as used in Example 1 until the alumina spherical granules are wholly dipped. Thereafter, the resultant is treated in the same manner as described in Example 1 to give a sintered product.

In the sintered product thus obtained, the round bar and the spherical granules are strongly bound.

EXAMPLE 4

A dense sintered plate of alumina [40×40 mm×5 mm (thickness)] having a concave portion [25×25 mm×1 mm (depth)] is used, and into the concave portion are filled spheres of dense sintered product of alumina (diameter: 1 mm) in one layer. Onto the filling layer of alumina is poured the same slurry a used in Example 1 until the alumina spheres are wholly dipped. Thereafter, the resultant is subjected to the dring and heating treatment in the same manner as described in Example 1 to give a sintered product. In said sintered product, the alumina spheres and the plate are strongly bound.

What is claimed is:

1. In a process for the production of a ceramic implant material having at least one layer of ceramic granules bonded on a surface thereof, which comprises arranging spherical granules of a ceramic material on at least a portion of a concave surface of a ceramic implant substrate to be bound to a living tissue in the form of at least one layer contacting the implant substrate and sintering the resultant product, the improvement comprising:

arranging the ceramic granules on the concave surface of the substrate such that contact points occur between the ceramic granules and the ceramic substrate and also between the ceramic granules themselves;

pouring slurry of a ceramic powder onto the surface of the substrate arranged with the granules whereby the granules are immersed in the slurry, and drying the slurry before sintering whereby the ceramic powder is concentrated and coagulated around the contact points occurring between the granules and the substrate and between the granules themselves;

said ceramic material for the ceramic granules and for the ceramic powder being the same as or similar to the material for the ceramic implant substrate, and said ceramic implant substrate and ceramic spherical granules being a dense sintered product of a ceramic material.

2. The process according to claim 1, wherein the ceramic substrate is composed of a member selected from the group consisting of alumina, zirconia, silicon nitride, and silicon carbide.

3. The process according to claim 1, wherein the ceramic spherical granules have a diameter of 0.3 mm to 5.0 mm.

4. The process according to claim 3, wherein the diameter of the ceramic spherical granules is in the range of 0.5 mm to 2.0 mm.

5. The process according to claim 1, wherein the ceramic powder has a particle size of not more than 5 $\mu$m.

6. The process to claim 1, wherein the slurry of a ceramic powder has a viscosity of 5 to 100 centipoise.

7. The process according to claim 1, wherein the ceramic spherical granules are arranged in the form of 1 to 10 layers.

* * * * *